United States Patent
Pelote

(10) Patent No.: US 9,433,480 B2
(45) Date of Patent: Sep. 6, 2016

(54) IMPLANT WITH POROUS SLEEVE INCLUDING ANTI-ROTATION FEATURES

(75) Inventor: Steven Pelote, Vista, CA (US)

(73) Assignee: Zimmer Dental, Inc., Carlsbad, CA (US)

( * ) Notice: Subject to any disclaimer, the term of this patent is extended or adjusted under 35 U.S.C. 154(b) by 575 days.

(21) Appl. No.: 12/974,830

(22) Filed: Dec. 21, 2010

(65) Prior Publication Data

US 2012/0156646 A1    Jun. 21, 2012

(51) Int. Cl.
*A61C 8/00* (2006.01)

(52) U.S. Cl.
CPC ............... *A61C 8/00* (2013.01); *A61C 8/0012* (2013.01); *A61C 8/0042* (2013.01)

(58) Field of Classification Search
CPC ..... A61C 8/00; A61C 8/0012; A61C 8/0042
USPC ........ 433/172–176, 201.1; 623/23.52–23.55, 623/17.17; 606/62–68, 300–321, 328
See application file for complete search history.

(56) References Cited

U.S. PATENT DOCUMENTS

| | | | | |
|---|---|---|---|---|
| 3,623,164 A | * | 11/1971 | Bokros | ........................... 606/60 |
| 3,906,550 A | * | 9/1975 | Rostoker et al. | .......... 623/23.55 |
| 3,934,347 A | * | 1/1976 | Lash et al. | .................... 433/173 |
| 4,011,602 A | * | 3/1977 | Rybicki et al. | ............. 623/23.76 |
| 4,259,072 A | * | 3/1981 | Hirabayashi et al. | ........ 433/173 |
| 4,424,037 A | * | 1/1984 | Ogino et al. | ................... 433/173 |
| 4,437,191 A | * | 3/1984 | van der Zel et al. | ...... 623/23.56 |
| 4,456,005 A | * | 6/1984 | Lichty | ............................. 606/60 |
| 4,790,852 A | * | 12/1988 | Noiles | ........................ 623/23.46 |
| 4,872,840 A | * | 10/1989 | Bori | ............................... 433/173 |
| 5,049,074 A | * | 9/1991 | Otani et al. | .................... 433/173 |
| 5,108,443 A | * | 4/1992 | Branemark | ................. 623/21.15 |
| 5,167,502 A | * | 12/1992 | Kawahara et al. | ............ 433/173 |
| 5,310,343 A | * | 5/1994 | Hasegawa et al. | ............ 433/173 |
| 5,360,448 A | * | 11/1994 | Thramann | ....................... 606/60 |
| 5,645,589 A | * | 7/1997 | Li | .................................... 606/60 |
| 6,099,312 A | * | 8/2000 | Alvaro | .......................... 433/174 |
| 6,168,633 B1 | * | 1/2001 | Shoher et al. | ............... 623/23.6 |

(Continued)

FOREIGN PATENT DOCUMENTS

| | | | | | |
|---|---|---|---|---|---|
| DE | | 4001183 A1 | * | 7/1991 | ............... A61C 8/00 |
| DE | | 4130891 A1 | * | 3/1992 | ............... A61C 8/00 |

(Continued)

OTHER PUBLICATIONS

English language machine translation of JP2880755B2, Apr. 1999.*

(Continued)

*Primary Examiner* — Cris L Rodriguez
*Assistant Examiner* — Mirayda A Aponte
(74) *Attorney, Agent, or Firm* — Schwegman Lundberg & Woessner, P.A.

(57) ABSTRACT

A modular dental implant including a body portion, a sleeve, and an end cap. The sleeve may be formed of porous material, such as a porous metal material to promote bone ingrowth. The sleeve is positionable around a core of the body portion and the end cap is attached to the core of the body portion such that the sleeve is positioned between the head of the body portion and the end cap. The sleeve includes one or more anti-rotation features formed in the upper surface and/or lower surface of the sleeve configured to interact with one or more anti-rotation features formed in the lower surface of the head of the body portion and/or the upper surface of the end cap which prevent rotation of the sleeve relative to the core of the body portion.

15 Claims, 14 Drawing Sheets

(56) References Cited

U.S. PATENT DOCUMENTS

| | | | |
|---|---|---|---|
| 6,174,167 B1 * | 1/2001 | Wohrle | 433/173 |
| 6,379,153 B1 * | 4/2002 | Schroering | 433/173 |
| 6,743,018 B1 * | 6/2004 | Morrow | 433/173 |
| 8,057,230 B1 * | 11/2011 | Folsom, Jr. | 433/174 |
| 2003/0031982 A1 * | 2/2003 | Abarno | 433/173 |
| 2003/0143514 A1 * | 7/2003 | Peltier | 433/173 |
| 2004/0170946 A1 * | 9/2004 | Lyren | 433/173 |
| 2004/0234925 A1 * | 11/2004 | Benhamou | 433/173 |
| 2007/0038219 A1 * | 2/2007 | Matthis | A61B 17/864 623/17.11 |
| 2007/0073295 A1 * | 3/2007 | Biedermann et al. | 606/62 |
| 2007/0293866 A1 * | 12/2007 | Stoeckel et al. | 606/72 |
| 2009/0076621 A1 * | 3/2009 | Rollet | 623/23.45 |
| 2010/0003640 A1 * | 1/2010 | Damstra | A61C 8/0012 433/201.1 |
| 2011/0123951 A1 * | 5/2011 | Lomicka | A61C 8/0012 433/174 |

FOREIGN PATENT DOCUMENTS

| | | | | | |
|---|---|---|---|---|---|
| DE | 19705571 A1 | * | 9/1998 | | A61C 8/00 |
| EP | 337759 A2 | * | 10/1989 | | A61C 8/00 |
| JP | 02017062 A | * | 1/1990 | | A61F 2/28 |
| JP | 02121654 A | * | 5/1990 | | A61C 8/00 |
| JP | 03292947 A | * | 12/1991 | | A61C 8/00 |
| JP | 03292948 A | * | 12/1991 | | A61C 8/00 |
| JP | 03292949 A | * | 12/1991 | | A61C 8/00 |
| JP | 04183463 A | * | 6/1992 | | A61C 8/00 |
| JP | 05064647 A | * | 3/1993 | | A61C 8/00 |
| JP | 05305132 A | * | 11/1993 | | A61L 27/00 |
| JP | 2880755 B2 | * | 4/1999 | | |
| WO | WO 2010/002661 A2 | | 1/2010 | | |
| WO | WO 2010062090 A2 | * | 6/2010 | | A61C 8/00 |
| WO | WO 2010/106241 A2 | | 9/2010 | | |
| WO | WO-2012087390 A9 | | 6/2012 | | |

OTHER PUBLICATIONS

International Search Report and Written Opinion issued on related PCT Application No. PCT/US11/51701; report dated Jan. 9, 2012.
"International Application Serial No. PCT/US2011/051701, International Preliminary Report on Patentability mailed Jul. 4, 2013", 9 pgs.

* cited by examiner

IMPLANT WITH POROUS SLEEVE INCLUDING ANTI-ROTATION FEATURES

TECHNICAL FIELD

The disclosure is directed to bone implants, such as dental implants. More particularly, the disclosure is directed to dental implants with structure for securing a porous portion to the implant.

BACKGROUND

Dental implants are commonly used as anchoring members for dental restorations. The dental implant is typically threaded or press fit into a bore which is drilled into the patient's mandible or maxilla. The implant provides an anchoring member for a dental abutment, which in turn provides an interface between the implant and a dental restoration. Known implant systems include a dental implant made from a suitable biocompatible material, such as titanium. The implant provides an interface between the implant and a dental restoration. The restoration is typically a porcelain crown fashioned according to known methods.

One way to improve osseointegration into the implant, and in turn long term stability of the implant, is to provide a porous material on the implant that the bone can grow into. Some examples of the inclusion of a porous material on a dental implant are described in U.S. Pat. App. Pub. Nos. 2008/0241793, 2009/0011384, 2010/0003638, and 2010/0003640, the disclosures of which are incorporated herein by reference. Securing the porous material to the dental implant, however, may be difficult. Accordingly, it may be desirable to provide alternative configurations to enhance securement of the porous material to the dental implant.

SUMMARY

The disclosure is directed to several alternative designs, materials and methods of manufacturing medical device structures and assemblies.

Accordingly, one illustrative embodiment is a modular dental implant including a body portion and a sleeve. The body portion includes head portion and a reduced diameter core extending from the head portion. The sleeve includes a bore extending therethrough from an upper surface of the sleeve to a lower surface of the sleeve. The sleeve is positionable around the reduced diameter core of the body portion with the upper surface of the sleeve facing the head portion. The upper surface of the sleeve does not reside in a single plane perpendicular to the central longitudinal axis of the body portion.

Another illustrative embodiment is a modular dental implant including a body, a sleeve, and an end cap. The body includes a head portion and a core extending from the head portion. The sleeve includes a bore extending therethrough from an upper surface of the sleeve to a lower surface of the sleeve. The sleeve is positionable around the core of the body such that the upper surface of the sleeve faces a lower surface of the head portion of the body. The end cap is attached to the core of the body such that the sleeve is captured between the head portion and the end cap. The modular dental implant includes means for preventing rotation of the sleeve about the central longitudinal axis of the body relative to the core of the body.

Yet another illustrative embodiment is a method of assembling a modular dental implant. The method includes providing a body including a head portion and a core extending from the head portion. A sleeve is advanced over the core such that an upper surface of the sleeve engages a lower surface of the head portion. The upper surface of the sleeve is mated with the lower surface of the head portion to prevent rotation of the sleeve relative to the core of the body.

The above summary of some example embodiments is not intended to describe each disclosed embodiment or every implementation of the invention.

BRIEF DESCRIPTION OF THE DRAWINGS

The invention may be more completely understood in consideration of the following detailed description of various embodiments in connection with the accompanying drawings, in which.

Figure 1:
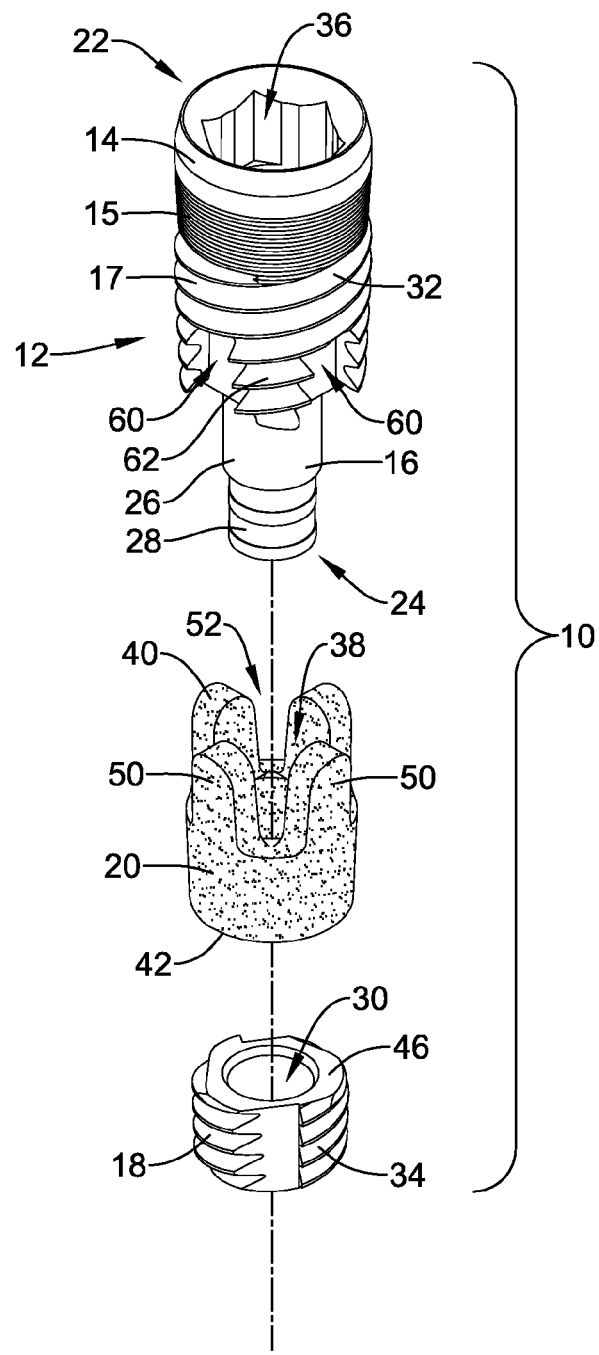
FIG. 1 is an exploded perspective view of an exemplary modular dental implant.

While the invention is amenable to various modifications and alternative forms, specifics thereof have been shown by way of example in the drawings and will be described in detail. It should be understood, however, that the intention is not to limit aspects of the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the invention. The illustrative embodiments depicted are intended only as exemplary. Selected features of any illustrative embodiment may be incorporated into an additional embodiment unless clearly stated to the contrary.

Figure 2:
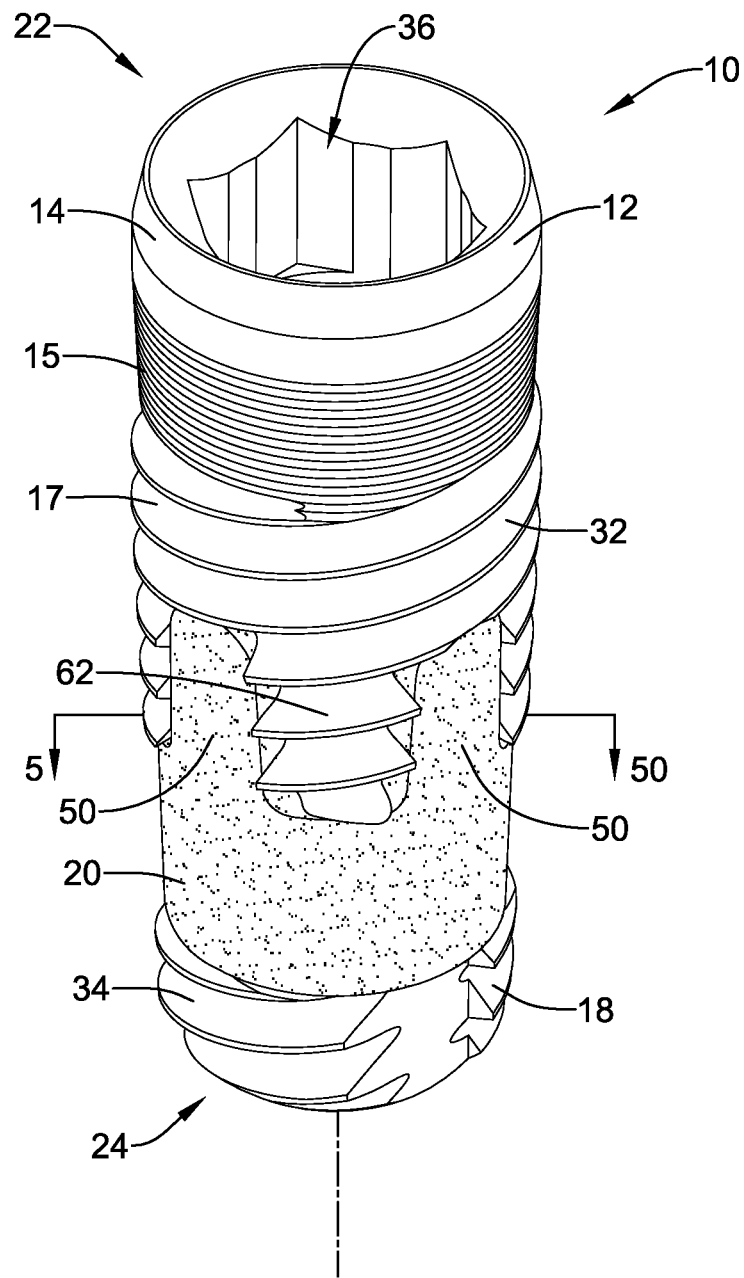
FIG. 2 is an assembled perspective view of the exemplary modular dental implant of FIG. 1.

Referring to FIGS. 1 and 2, there is shown an implant 10 for placement in bone, which in one form may be a dental implant for insertion into a mandible or maxilla. The implant 10 may be used to anchor a tooth abutment or other dental prosthesis.

The implant 10 may be in modular form, including a plurality of assembled components. For example, the implant 10 may include a body portion 12, a sleeve 20, and an end cap 18 formed as separate components and subsequently assembled together to form the implant 10. In some instances, the implant 10 may include a different number of components, such as fewer or additional components, which may be assembled together to form the implant 10.

The body portion 12 may be a unitary member formed of a biocompatible material, such as titanium or stainless steel, for example. The body portion 12, beginning at the proximal or coronal end 22 of the implant 10 and moving toward the distal or apical end 24 of the implant 10, may include a head portion 14, having an upper portion 15 and a lower portion 17, and a core 16 extending from the head portion 14 and the upper portion 15. The core 16 may be a reduced diameter portion relative to the head portion 14. The core 16 may include a larger diameter portion 26 toward the coronal end 22 and proximate the head portion 14, transitioning to a smaller diameter portion 28 proximate the apical end 24. Thus, the distal or apical portion of the core 16 may have a diameter less than the proximal or coronal portion of the core 16.

The head portion 14 may include an engagement structure 36 which may be configured to receive a driver for rotationally inserting the implant 10 in a bone. For example, the proximal end of the head portion 14 may include an internal hex for receiving a hex driver therein, or another driver interface such as splines, octagons, lobes, torx, other geometric shapes, and other engaging configurations.

Figure 3:
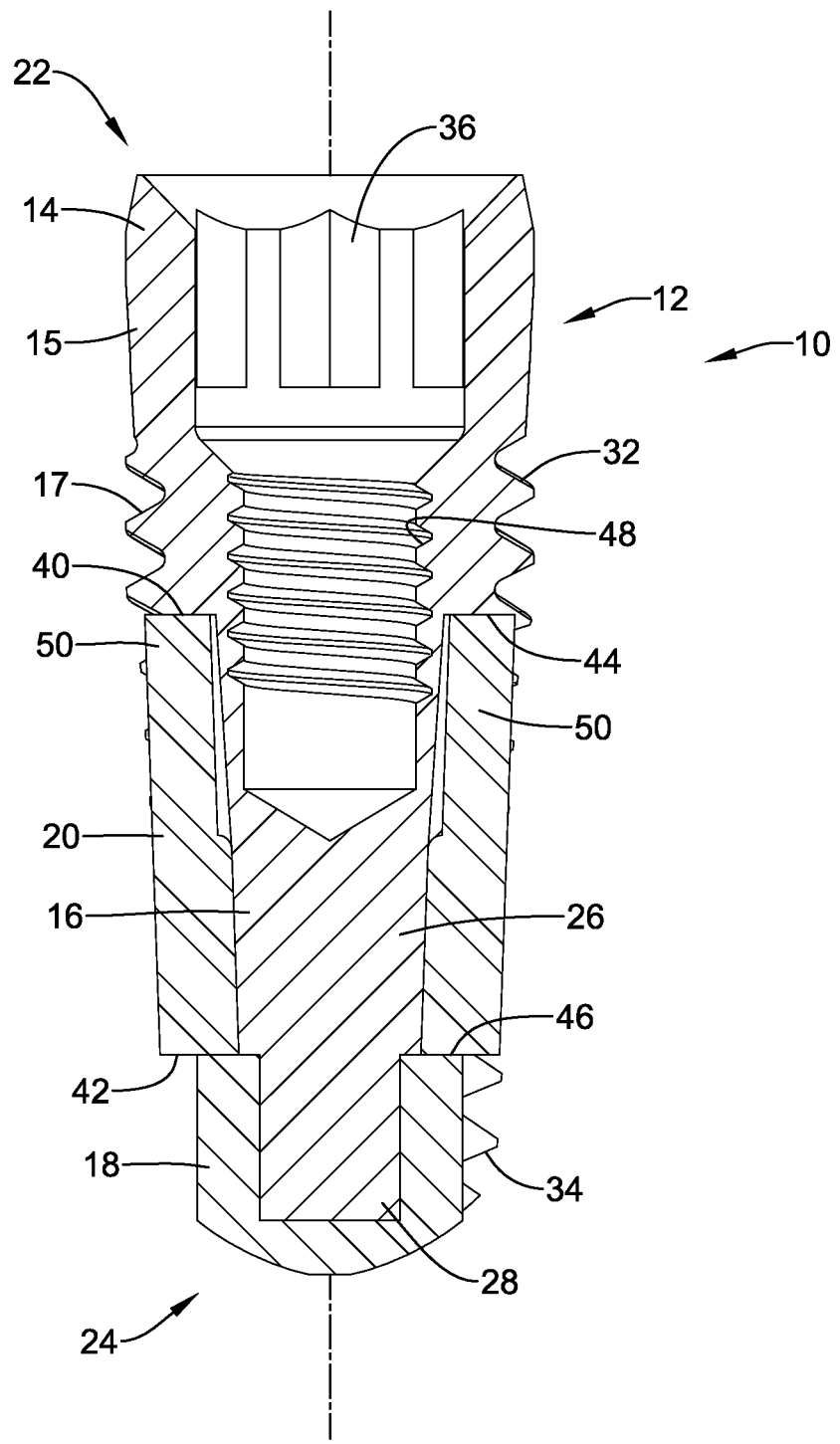
FIG. 3 is a longitudinal cross-sectional view of the assembled modular dental implant of FIG. 2.
Figure 4:
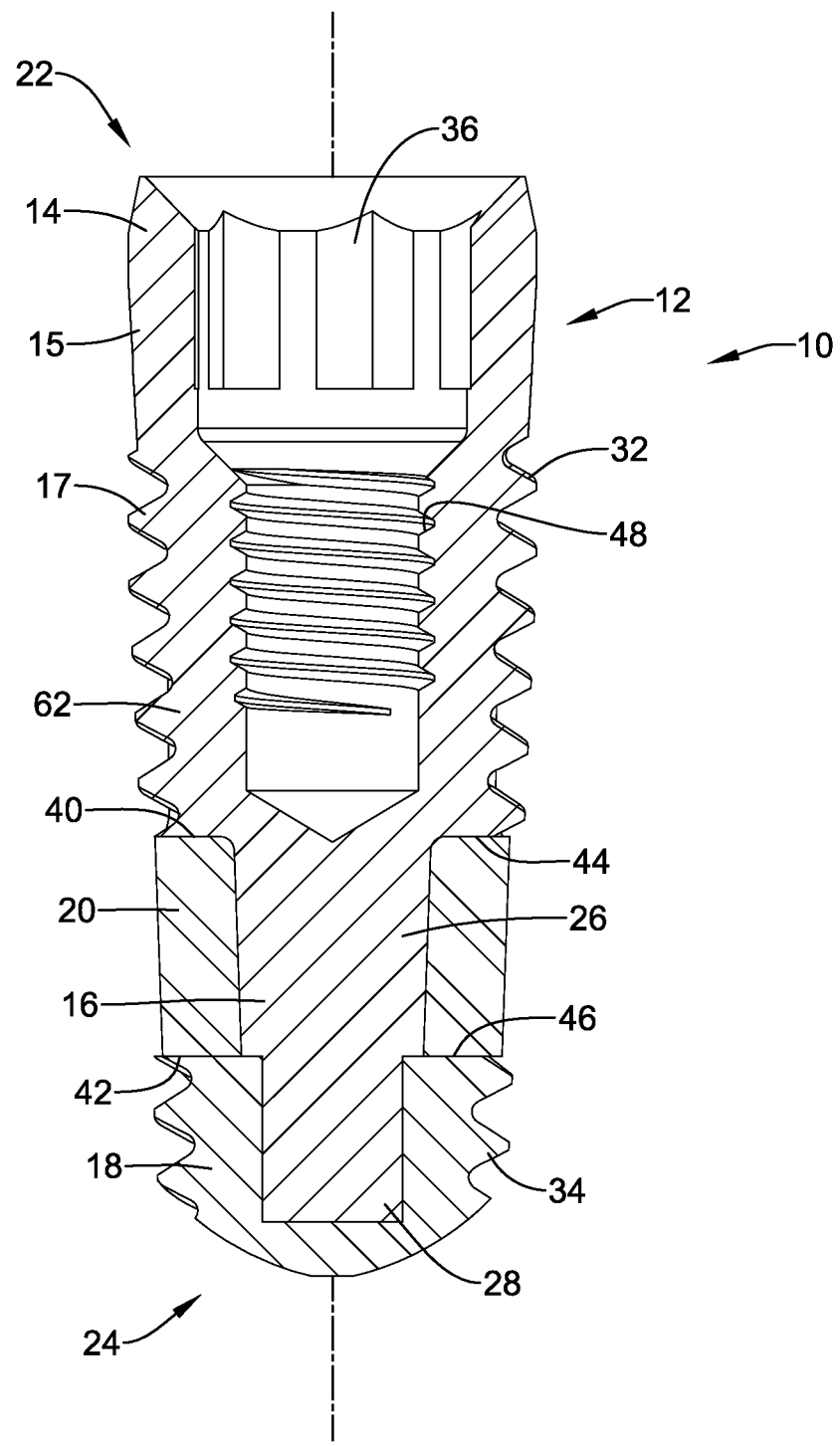
FIG. 4 is another longitudinal cross-sectional view of the assembled modular dental implant of FIG. 2.

Furthermore, the body portion 12 may include an internally threaded portion 48 of the bore of the body portion 12, as shown in FIGS. 3 and 4, for threadably engaging a component of an abutment to attach an abutment to the implant 10.

The head portion 14 may include external threads 32 for engaging bone. In some embodiments threading of the upper portion 15 of the head portion 14 may be similar or dissimilar to threading of the lower portion 17 of the head portion 14. The threads 32 may provide initial stability of the implant 10 when implanted in a bone prior to osseointegration in some instances.

The sleeve 20 may be an annular sleeve having a bore 38 extending therethrough from an upper end surface 40 to a lower end surface 42 of the sleeve 20. The sleeve 20 may be generally cylindrical, but in some instances may taper to generally match the taper of the implant 10, if desired. The sleeve 20 may be positionable about or surrounding the core 16 of the body portion 12 such that the core 16 of the body portion 12 extends through the bore 38 of the sleeve 20. For example, the sleeve 20 may surround the larger diameter portion 26 of the core 16 with the smaller diameter portion 28 extending from the lower end surface 42 of the sleeve 20.

In some embodiments, the sleeve 20 may be formed of a porous material, such as a porous metal material configured to promote ingrowth of bone or soft tissue therein to improve osseointegration onto the implant 10, resulting in long term stability of the implant 10 in bone. Such a porous material may also increase short term stability of the implant 10 due to the frictional engagement of the porous material of the sleeve 20 with the surrounding bone. The porous material may mimic the microstructure of a natural cancellous bone, acting as an osteoconductive matrix for the incorporation of bone, providing optimal permeability and high surface area to encourage new bone ingrowth into the pores of the porous scaffold of the porous material.

One exemplary porous metal material is Trabecular Metal™ material, which is a porous tantalum material marketed by Zimmer Spine, Inc. of Minneapolis, Minn. This material is also disclosed in several U.S. patents, including, for example, U.S. Pat. Nos. 5,282,861, 5,443,515, and 6,063,442, the disclosures of which are incorporated herein by reference. These patents describe the formation of a tantalum porous structure by chemical vapor deposition of tantalum onto a foam carbon structure.

The end cap 18 may be a unitary member formed of a biocompatible material, such as titanium or stainless steel, for example. The end cap 18 may be securable to the core 16 of the body portion 12 proximate the apical end 24 of the implant 10 to retain the sleeve 20 between the head portion 14 and the end cap 18. For example, the end cap 18 may include a bore 30 extending therein or therethrough for receiving the smaller diameter portion 28 of the core 16 therein. The end cap 18 may be secured to the core 16 by a threaded connection, press fit, adhesive, welding, diffusion bonding, sintering, crimping, swaging, fasteners, or similar mechanisms.

The end cap 18 may include external threads 34 for engaging bone. In some embodiments the threads 34 may be self-tapping threads. The threads 34 may provide initial stability of the implant 10 when implanted in a bone prior to osseointegration in some instances.

As shown in FIGS. 3 and 4, with the sleeve 20 assembled around the larger diameter portion 26 of the core 16, the end cap 18 may be secured to the smaller diameter portion 28 of the core 16, capturing the sleeve 20 between a lower surface 44 of the head 14 and an upper surface 46 of the end cap 18. Thus, the upper end surface 40 of the sleeve 20 may face and/or abut the lower rim or surface 44 of the head 14 and the lower end surface 42 of the sleeve 20 may face and/or abut the upper surface 46 of the end cap 18, preventing subsequent removal of the sleeve 20 from the body portion 12.

The sleeve 20 may include one or more anti-rotation features configured to interact with one or more anti-rotation features of the body portion 12 which prevent rotation of the sleeve 20 about the central longitudinal axes of the body portion 12 and sleeve 20 relative to the core 16 of the body portion 12. For example, the sleeve 20 may include an anti-rotation feature formed in the upper surface 40 of the sleeve 20 configured to mate with an anti-rotation feature formed in the lower surface 44 of the head 14 of the body portion 12.

For example, in some embodiments the upper surface 40 of the sleeve 20 does not reside in a single plane perpendicular to the central longitudinal axis of the body portion 12. In some instances, the upper surface 40 of the sleeve 20 may be a non-planar surface interacting with the lower surface 44 (which may be a non-planar surface) of the head portion 14 of the body portion 12 to prevent rotation of the sleeve 20 relative to the core 16 of the body portion 12. For instance, as shown in FIGS. 1 and 2, the upper surface 40 of the sleeve 20 may include one or more, or a plurality of projecting portions, such as fingers 50 configured to extend into one or more, or a plurality of corresponding recesses 60 formed in the head portion 14. The mating relationship between the fingers 50 and the recesses 60 may prevent rotation of the sleeve 20 relative to the core 16 of the body portion 12 when assembled.

Accordingly, the upper surface 40 of the sleeve 20 may include one or more, or a plurality of peaks (e.g., the fingers 50) and valleys (e.g., openings or depressions 52). The peaks being portions of the upper surface 40 which are closer to the proximal or coronal end 22 of the implant 10 and the valleys being portions of the upper surface 40 which are closer to the distal or apical end 24 of the implant 10. The fingers 50 and depressions 52 may be alternatingly arranged around the circumference of the sleeve 20.

The head portion 14 may include lands 62, which may be threaded portions of the head portion 14, which are alternatingly arranged circumferentially between recesses 60 formed in the head portion 14. In some instances, the recesses 60 may be formed by removing material from the head portion 14 subsequent to forming threads 32 in the head portion 14, leaving the lands 62. When assembled, as shown in FIG. 2, the threaded portions or lands 62 of the head portion 14 may be positioned closer to the lower surface 42 of the sleeve 20 (and thus closer to the apical end 24) than portions of the upper surface 40 of the sleeve 20.

When the sleeve 20 is assembled with the body portion 12, the fingers 50 may extend into the recesses 60 of the head portion 14, while the depressions 52 of the sleeve 20 receive the lands 62 of the head portion 14 therein. The resulting mating relationship between the sleeve 20 and the head portion 14 may prevent rotation of the sleeve 20 relative to the core 16 of the body portion 12 when assembled.

FIG. 3 is a longitudinal cross-sectional view of the implant 10 taken through the fingers 50 of the sleeve 20, while FIG. 4 is a longitudinal cross-sectional view of the implant 10 taken through the lands 62 of the head portion 14. As can be seen from these figures, portions of the sleeve 20 overlap with portions of the head portion 14 such that portions of the sleeve 20 are closer to the coronal end 22 of the implant 10 than portions of the head portion 14, and likewise, portions of the head portion 14 extend closer to the apical end 24 of the implant 10 than portions of the sleeve 20.

Figure 5:
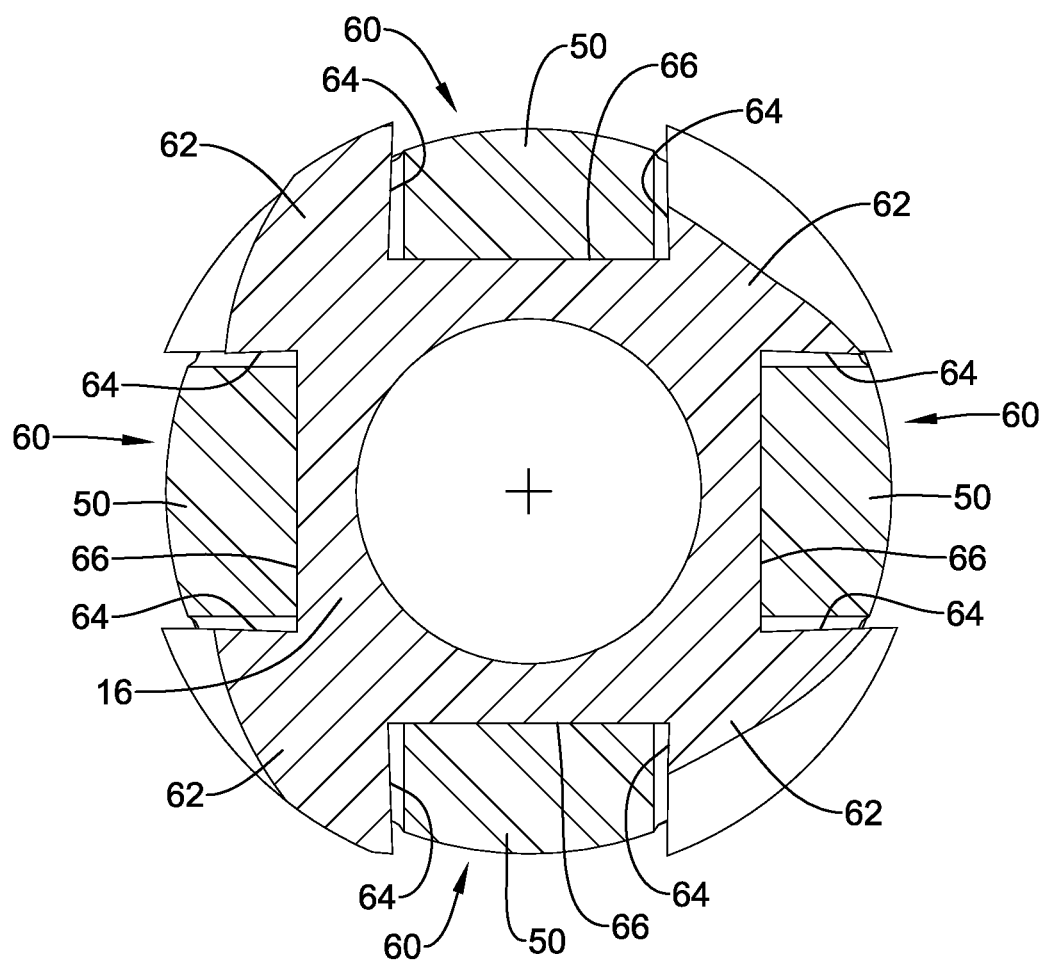
FIG. 5 is a transverse cross-sectional view of the modular dental implant of FIG. 2 taken along line 5-5.

FIG. 5 is a cross-sectional view illustrating the mating relationship between the fingers 50 of the sleeve 20 and the recesses 60 of the head portion 14 of the body portion 12, when the sleeve 20 is assembled around the core 16. As shown, the recesses 60 formed in the head portion 14 of the body portion 12 are shaped and sized to mate with and receive the fingers 50 defined in the upper surface 40 of the sleeve 20. The intermeshing engagement between the fingers 50 of the sleeve 20 and the recesses 60 of the head portion 14 may prevent rotation of the sleeve 20 relative to the core 16 about the central longitudinal axis of the implant 10. As shown in FIG. 5, a cross-section of the implant 10 taken perpendicular to the central longitudinal axis includes one or more portions (e.g., the lands 62) of the head portion 14 alternatingly arranged with one or more portions (e.g., the fingers 50) of the sleeve 20 circumferentially about the longitudinal axis radially outward of the outer diameter of the core 16.

As shown in FIG. 5, the fingers 50 may be positioned in the recesses 60 such that the fingers 50 are bound by the side surfaces 64 of the recesses 60 and the inner surface 66 of the recesses 60. Thus, engagement with the side surfaces 64 of the recesses 60 will prevent rotation of the sleeve 20 relative to the core 16 of the body portion 12.

In assembling the implant 10, the sleeve 20 may be rotationally oriented in alignment with the core 16 such that the geometry of the upper surface 40 of the sleeve 20 is aligned with the geometry of the lower surface 44 of the head portion 14. Then the sleeve 20 may be advanced over the larger diameter portion 26 of the core 16 parallel to the central longitudinal axis of the implant 10 such that the geometry of the upper surface 40 of the sleeve 20 mates with the geometry of the lower surface 44 of the head portion 14 to prevent rotation of the sleeve 20 relative to the core 16. Accordingly, the portions of the upper surface 40 of the sleeve 20 are aligned with and engage the complementary portions of the lower surface 44 of the head portion 14. Thereafter, the end cap 18 may be attached to the core 16 of the body portion 12 to capture the sleeve 20 between the head portion 14 of the body portion 12 and the end cap 18 to prevent subsequent removal of the sleeve 20 from the core 16.

Figure 6:
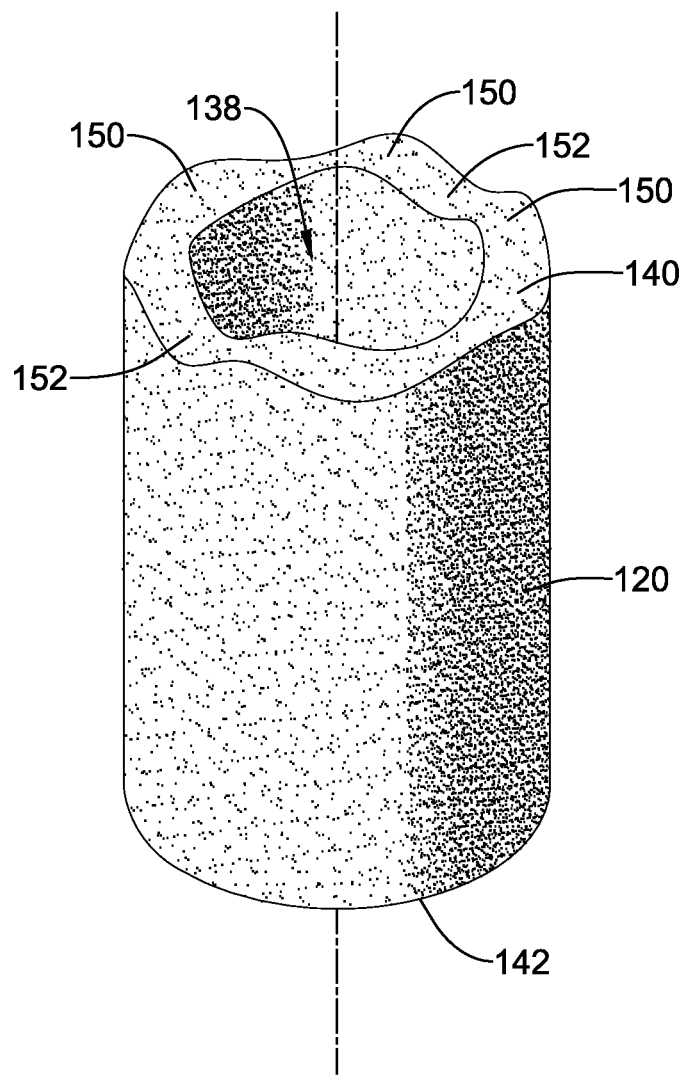
FIG. 6 is a perspective view of an alternative sleeve of a modular dental implant.

FIG. 6 is a perspective view of an alternative sleeve 120 of a modular dental implant which is configured to mate with a head portion of the modular implant to prevent relative rotation therebetween. The sleeve 120 may include an upper surface 140, a lower surface 142, and a bore 138 extending therethrough from the upper surface 140 to the lower surface 142.

Similar to the sleeve 20, the upper surface 140 of the sleeve 120 may be a non-planar surface interacting with the lower surface 44 (which may be a non-planar surface) of the head portion 14 of the body portion 12 to prevent rotation of the sleeve 120 relative to the core 16 of the body portion 12. For instance, as shown in FIG. 6, the upper surface 140 of the sleeve 120 is a wavy surface defined by alternating peaks 150 and valleys 152 around the circumference of the sleeve 120 which may be configured to interact with a complementary wavy lower surface 44 of the head portion 14. The peaks 150 being portions of the upper surface 140 which are closer to the proximal or coronal end 22 of the implant 10 and the valleys 152 being portions of the upper surface 140 which are closer to the distal or apical end 24 of the implant 10. The mating relationship between the peaks 150 and valleys 152 of the wavy upper surface 140 of the sleeve 120 with cooperating peaks and valleys of a wavy surface of the lower surface 44 of the head portion 14 may prevent rotation of the sleeve 120 relative to the core 16 of the body portion 12 when assembled. Accordingly, portions of the sleeve 120 may be closer to the coronal end 22 of the implant 10 than portions of the head portion 14, and likewise, portions of the head portion 14 may extend closer to the apical end 24 of the implant 10 than portions of the sleeve 120.

Figure 7:
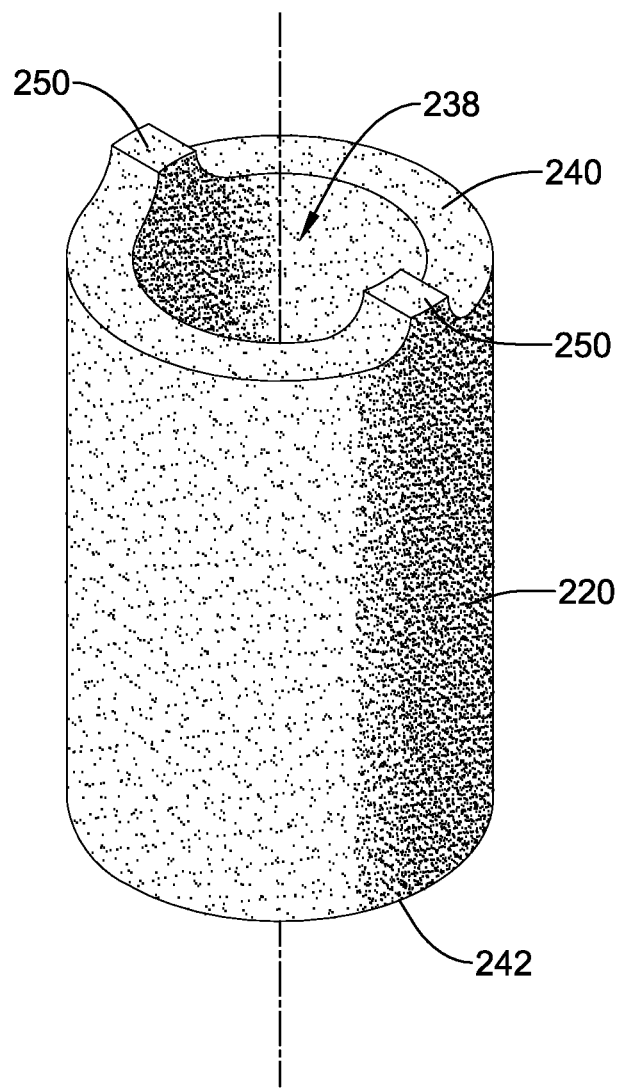
FIG. 7 is a perspective view of another alternative sleeve of a modular dental implant.

FIG. 7 is a perspective view of another alternative sleeve 220 of a modular dental implant which is configured to mate with a head portion of the modular implant to prevent relative rotation therebetween. The sleeve 220 may include an upper surface 240, a lower surface 242, and a bore 238 extending therethrough from the upper surface 240 to the lower surface 242.

Similar to the sleeve 20, the upper surface 240 of the sleeve 220 may include a non-planar surface interacting with the lower surface 44 (which may include a non-planar surface) of the head portion 14 of the body portion 12 to prevent rotation of the sleeve 220 relative to the core 16 of the body portion 12. For instance, as shown in FIG. 7, the upper surface 240 of the sleeve 220 may include one or more, or a plurality of projections 250 extending toward the coronal end 22 of the implant 10 relative to other portions of the upper surface 240. The projections 250, which may be positioned at desired intervals around the circumference of the sleeve 220, may be configured to interact with complementary recesses, openings, notches or grooves in the lower surface 44 of the head portion 14. The projections 250 being portions of the upper surface 240 which are closer to the proximal or coronal end 22 of the implant 10 than other portions of the upper surface 240 which are closer to the distal or apical end 24 of the implant 10. The mating relationship between projections 250 of the sleeve 220 with cooperating recesses, openings, notches or grooves in the lower surface 44 of the head portion 14 may prevent rotation of the sleeve 220 relative to the core 16 of the body portion 12 when assembled. Accordingly, portions of the sleeve 220 may be closer to the coronal end 22 of the implant 10 than portions of the head portion 14, and likewise, portions of the head portion 14 may extend closer to the apical end 24 of the implant 10 than portions of the sleeve 220.

Figure 8:
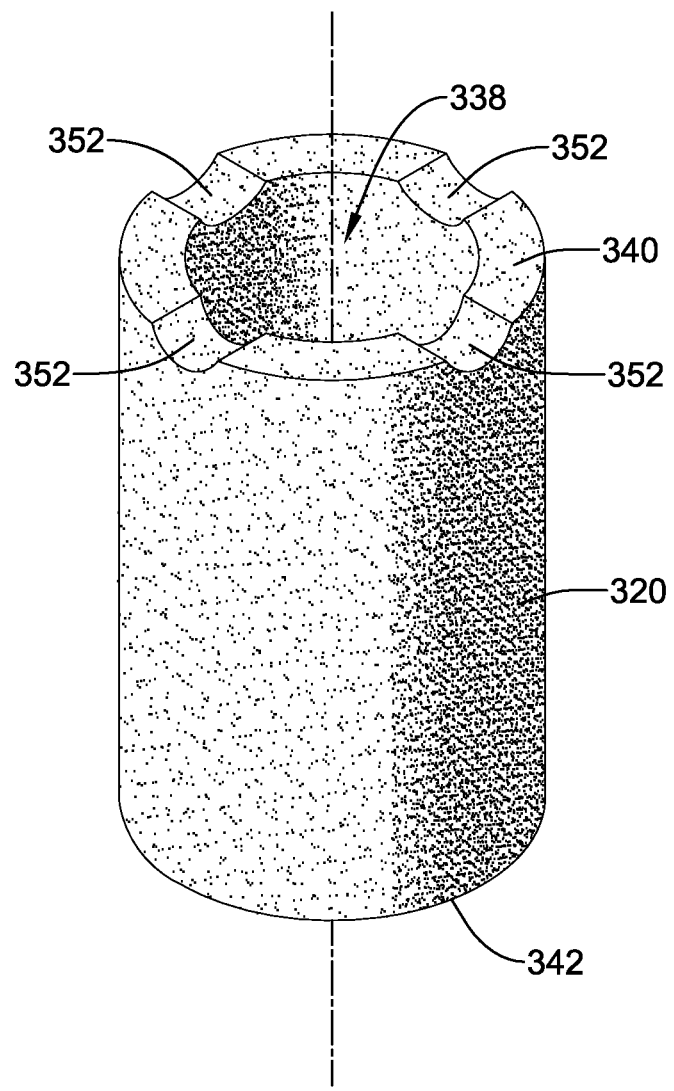
FIG. 8 is a perspective view of another alternative sleeve of a modular dental implant.

FIG. 8 is a perspective view of another alternative sleeve 320 of a modular dental implant which is configured to mate with a head portion of the modular implant to prevent relative rotation therebetween. The sleeve 320 may include an upper surface 340, a lower surface 342, and a bore 338 extending therethrough from the upper surface 340 to the lower surface 342.

Similar to the sleeve 20, the upper surface 340 of the sleeve 320 may include a non-planar surface interacting with the lower surface 44 (which may include a non-planar surface) of the head portion 14 of the body portion 12 to prevent rotation of the sleeve 320 relative to the core 16 of the body portion 12. For instance, as shown in FIG. 8, the upper surface 340 of the sleeve 320 may include one or more, or a plurality of divots or indentations 352 extending toward the apical end 24 of the implant 10 relative to other portions of the upper surface 340. The indentations 352, which may be positioned at desired intervals around the circumference of the sleeve 320, may be configured to interact with complementary tabs, bumps or projections in the lower surface 44 of the head portion 14. The indentations 352 being portions of the upper surface 340 which are closer to the distal or apical end 24 of the implant 10 than other portions of the upper surface 340 which are closer to the proximal or coronal end 22 of the implant 10. The mating relationship between indentations 352 of the sleeve 320 with cooperating tabs, bumps or projections in the lower surface 44 of the head portion 14 may prevent rotation of the sleeve 320 relative to the core 16 of the body portion 12 when assembled. Accordingly, portions of the sleeve 320 may be closer to the coronal end 22 of the implant 10 than portions of the head portion 14, and likewise, portions of the head portion 14 may extend closer to the apical end 24 of the implant 10 than portions of the sleeve 320.

Figure 9:
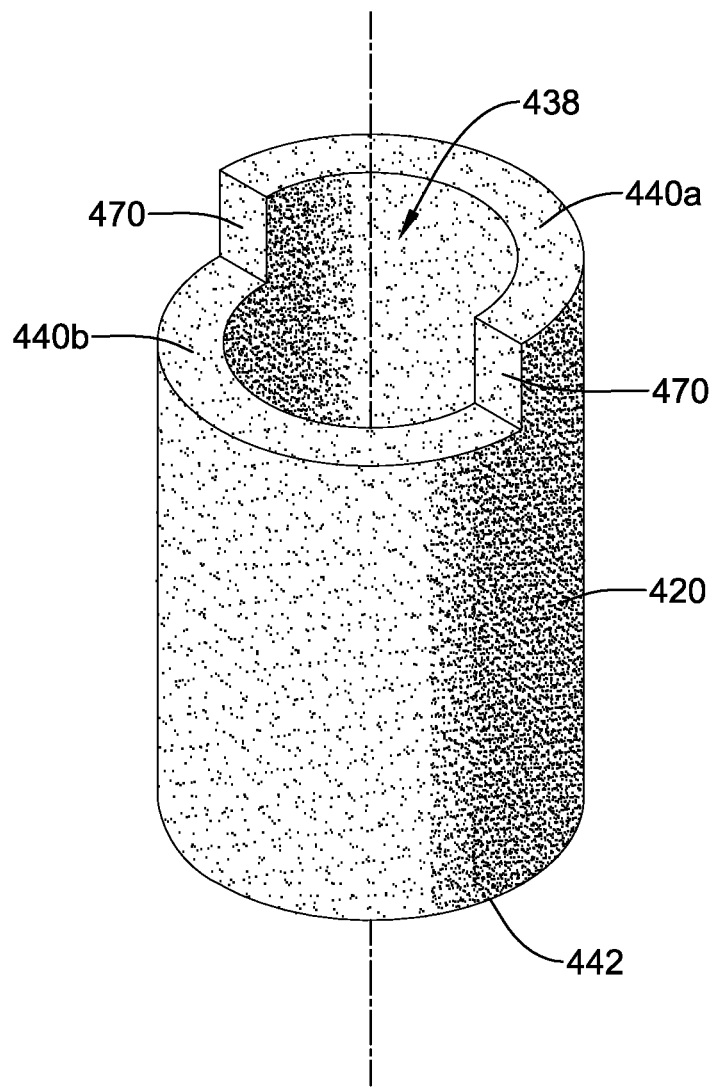
FIG. 9 is a perspective view of another alternative sleeve of a modular dental implant.

FIG. 9 is a perspective view of another alternative sleeve 420 of a modular dental implant which is configured to mate with a head portion of the modular implant to prevent relative rotation therebetween. The sleeve 420 may include an upper surface 440, a lower surface 442, and a bore 438 extending therethrough from the upper surface 440 to the lower surface 442.

Similar to the sleeve 20, the upper surface 440 of the sleeve 420 may not reside in a single plane and be configured for interacting with the lower surface 44 (which may not reside in a single plane) of the head portion 14 of the body portion 12 to prevent rotation of the sleeve 420 relative to the core 16 of the body portion 12. For instance, as shown in FIG. 9, the upper surface 440 of the sleeve 420 may include one or more, or a plurality of stepped portions 470 between other portions of the upper surface 440. For example, the upper surface 440 may include stepped portions 470 forming a transition between non-coplanar portions of the upper surface 440, such that a first portion 440$a$ of the upper surface 440 resides in a first plane which may be perpendicular to the central longitudinal axis in some instances, and a second portion 440$b$ of the upper surface 440 resides in a second plane (different from the first plane) which may be perpendicular to the central longitudinal axis in some instances. In some instances, the stepped portions 470 may be parallel to the central longitudinal axis, or the stepped portions 470 may be at an oblique angle to the central longitudinal axis. The stepped portions 470 of the upper surface 440, which may be positioned at desired intervals around the circumference of the sleeve 420, may be configured to interact with complementary stepped portions, tabs, bumps or projections in the lower surface 44 of the head portion 14. The stepped portions 470 provide the sleeve 420 with portions of the upper surface 440 which are closer to the distal or apical end 24 of the implant 10 than other portions of the upper surface 440 which are closer to the proximal or coronal end 22 of the implant 10. The mating relationship between stepped portions 470 of the sleeve 420 with cooperating stepped portions, tabs, bumps or projections in the lower surface 44 of the head portion 14 may prevent rotation of the sleeve 420 relative to the core 16 of the body portion 12 when assembled. Accordingly, portions of the sleeve 420 may be closer to the coronal end 22 of the implant 10 than portions of the head portion 14, and likewise, portions of the head portion 14 may extend closer to the apical end 24 of the implant 10 than portions of the sleeve 420.

Figure 10:
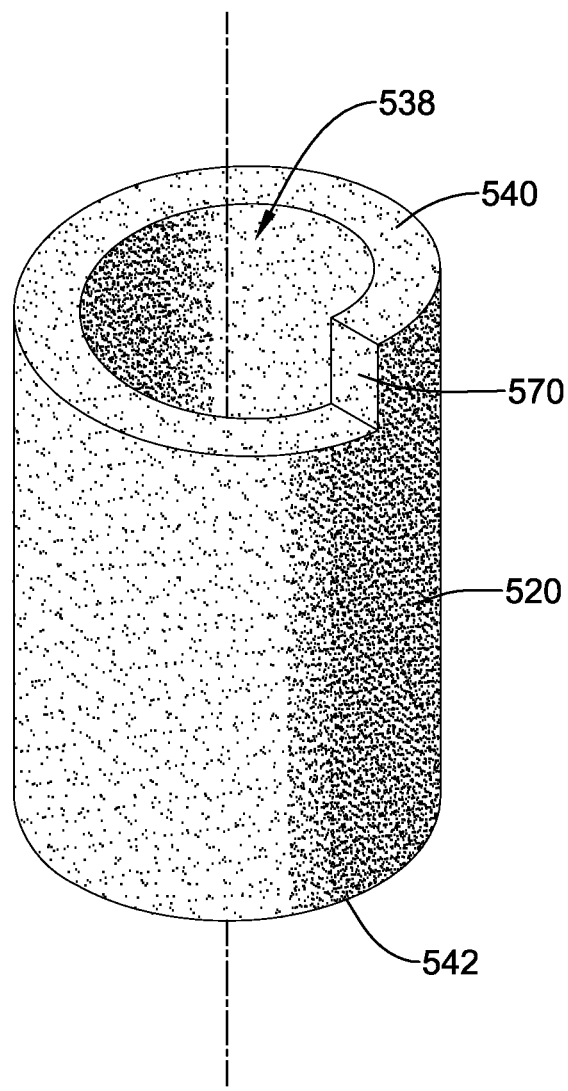
FIG. 10 is a perspective view of another alternative sleeve of a modular dental implant.

FIG. 10 is a perspective view of another alternative sleeve 520 of a modular dental implant which is configured to mate with a head portion of the modular implant to prevent relative rotation therebetween. The sleeve 520 may include an upper surface 540, a lower surface 542, and a bore 538 extending therethrough from the upper surface 540 to the lower surface 542.

Similar to the sleeve 20, the upper surface 540 of the sleeve 520 may not reside in a single plane perpendicular to the central longitudinal axis of the body portion 12 and be configured for interacting with the lower surface 44 (which may not reside in a single plane perpendicular to the central longitudinal axis of the body portion 12) of the head portion 14 of the body portion 12 to prevent rotation of the sleeve 520 relative to the core 16 of the body portion 12. For instance, as shown in FIG. 10, the upper surface 540 of the sleeve 520 may include one or more, or a plurality of stepped portions 570 between other portions of the upper surface 540. For example, the upper surface 540 may extend in a helical manner with the stepped portion 570 interconnecting portions of the helical upper surface 540 which reside in different planes and at different axial locations along the central longitudinal axis. In some instances, the stepped portion 570 may be parallel to the central longitudinal axis, or the stepped portion 570 may be at an oblique angle to the central longitudinal axis. The stepped portion 570 of the upper surface 540, which may be positioned at any desired position around the circumference of the sleeve 520, may be configured to interact with a complementary stepped portion, tab, bump or projection in the lower surface 44 of the head portion 14. The helical upper surface 540 and stepped portion 570 provides the sleeve 520 with portions of the upper surface 540 which are closer to the distal or apical end 24 of the implant 10 than other portions of the upper surface 540 which are closer to the proximal or coronal end 22 of the implant 10. The mating relationship between the helical upper surface 540 and stepped portion 570 of the sleeve 520 with a cooperating helical lower surface 44 of the head portion 14 and/or a stepped portion, tab, bump or projection in the lower surface 44 of the head portion 14 may prevent rotation of the sleeve 520 relative to the core 16 of the body portion 12 when assembled. Accordingly, portions of the sleeve 520 may be closer to the coronal end 22 of the implant 10 than portions of the head portion 14, and likewise, portions of the head portion 14 may extend closer to the apical end 24 of the implant 10 than portions of the sleeve 520.

Figure 11:
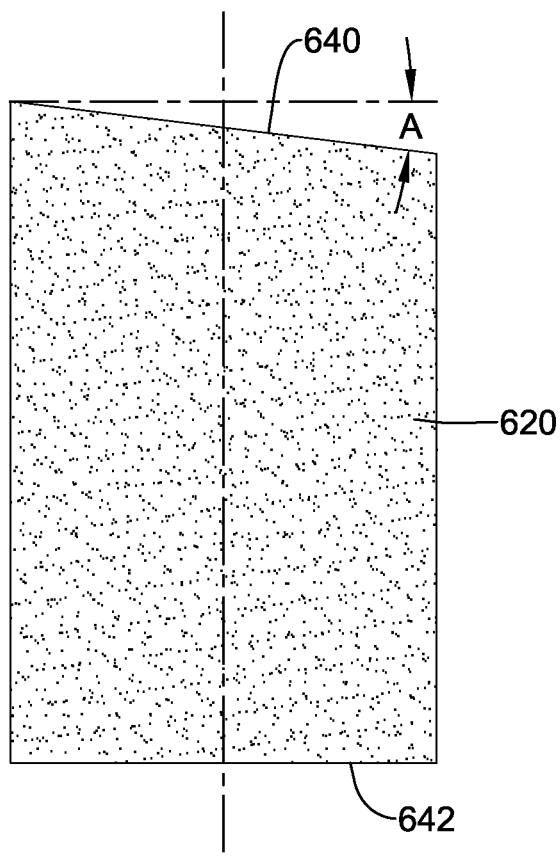
FIG. 11 is a side view of another alternative sleeve of a modular dental implant.

FIG. 11 is a side view of another alternative sleeve 620 of a modular dental implant which is configured to mate with a head portion of the modular implant to prevent relative rotation therebetween. The sleeve 620 may include an upper surface 640, a lower surface 642, and a bore (not shown) extending therethrough from the upper surface 640 to the lower surface 642.

In this embodiment, the upper surface 640 of the sleeve 620 may be a planar surface which is non-perpendicular to the central longitudinal axis of the implant 10 which may interact with the lower surface 44 (which may be a planar surface which is non-perpendicular to the central longitudinal axis of the implant 10) of the head portion 14 of the body portion 12 to prevent rotation of the sleeve 620 relative to the core 16 of the body portion 12. For instance, as shown in FIG. 11, the upper surface 640 of the sleeve 620 may be a planar surface residing in a plane which is at an oblique angle to the central longitudinal axis. For example, the planar upper surface 640 may be at an acute angle A to the central longitudinal axis. The angled upper surface 640 may be configured to interact with a complementary angled lower surface 44 of the head portion 14 which is non-perpendicular to the central longitudinal axis of the implant 10. The angled upper surface 640 provides the sleeve 620 with portions of the angled upper surface 640 which are closer to the distal or apical end 24 of the implant 10 than other portions of the angled upper surface 640 which are closer to the proximal or coronal end 22 of the implant 10. The mating relationship between the angled upper surface 640 of the sleeve 620 with a cooperating angled lower surface 44 of the head portion 14 may prevent rotation of the sleeve 620 relative to the core 16 of the body portion 12 when assembled. Accordingly, portions of the sleeve 620 may be closer to the coronal end 22 of the implant 10 than portions of the head portion 14, and likewise, portions of the head portion 14 may extend closer to the apical end 24 of the implant 10 than portions of the sleeve 620.

Figure 12:
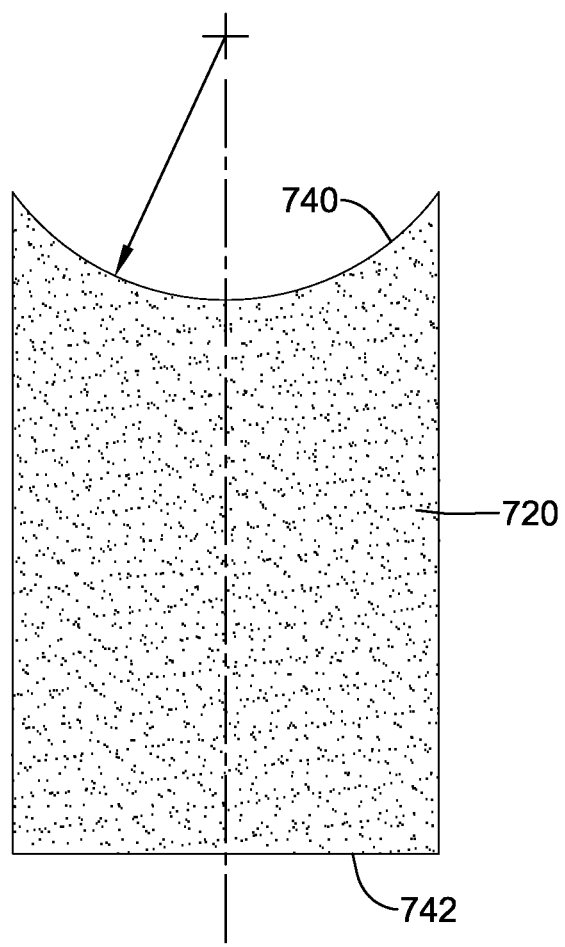
FIG. 12 is a side view of yet another alternative sleeve of a modular dental implant.

FIG. 12 is a side view of yet another alternative sleeve 720 of a modular dental implant which is configured to mate with a head portion of the modular implant to prevent relative rotation therebetween. The sleeve 720 may include an upper surface 740, a lower surface 742, and a bore (not shown) extending therethrough from the upper surface 740 to the lower surface 742.

In this embodiment, the upper surface 740 of the sleeve 720 may be an arcuate surface which is non-planar which may interact with the lower surface 44 (which may be an arcuate surface which is non-planar) of the head portion 14 of the body portion 12 to prevent rotation of the sleeve 720 relative to the core 16 of the body portion 12. For instance, as shown in FIG. 12, the upper surface 740 of the sleeve 720 may have a radius of curvature providing the upper surface with a curved profile when viewed perpendicular to the central longitudinal axis. The arcuate upper surface 740 may be configured to interact with a complementary arcuate lower surface 44 of the head portion 14 of the implant 10. The arcuate upper surface 740 provides the sleeve 720 with portions of the arcuate upper surface 740 which are closer to the distal or apical end 24 of the implant 10 than other portions of the arcuate upper surface 740 which are closer to the proximal or coronal end 22 of the implant 10. The mating relationship between the arcuate upper surface 740 of the sleeve 720 with a cooperating arcuate lower surface 44 of the head portion 14 may prevent rotation of the sleeve 720 relative to the core 16 of the body portion 12 when assembled. Accordingly, portions of the sleeve 720 may be closer to the coronal end 22 of the implant 10 than portions of the head portion 14, and likewise, portions of the head portion 14 may extend closer to the apical end 24 of the implant 10 than portions of the sleeve 720.

It is noted that although several embodiments described herein provide that the sleeve may include one or more anti-rotation features configured to interact with one or more anti-rotation features of the body portion 12 which prevent rotation of the sleeve about the central longitudinal axes of the body portion 12 and sleeve relative to the core 16 of the body portion 12, such as an anti-rotation feature formed in the upper surface of the sleeve configured to mate with an anti-rotation feature formed in the lower surface 44 of the head 14 of the body portion 12, it is contemplated that the sleeve may include one or more anti-rotation features, as described herein, configured to interact with one or more anti-rotation features of the end cap 18 which prevent rotation of the sleeve about the central longitudinal axes of the body portion 12 and sleeve relative to the core 16 of the body portion 12, such as an anti-rotation feature formed in the lower surface of the sleeve configured to mate with an anti-rotation feature formed in the upper surface 46 of the end cap 18 when the end cap 18 is secured to the body portion 12.

Figure 13:
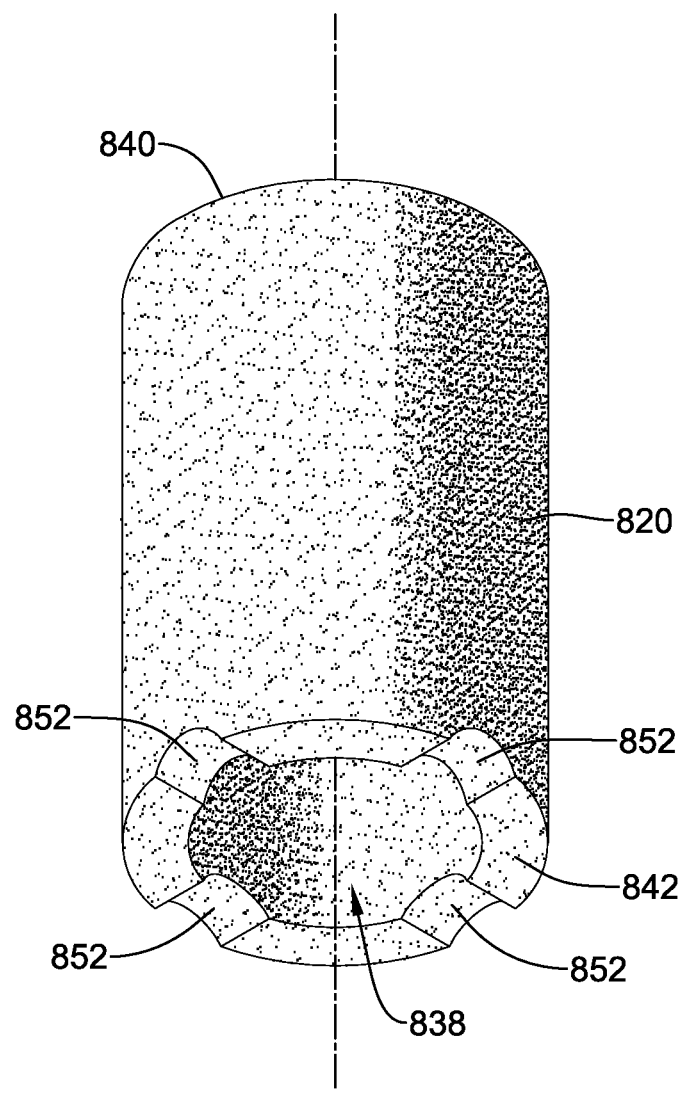
FIG. 13 is a perspective view of another alternative sleeve of a modular dental implant.
Figure 14:
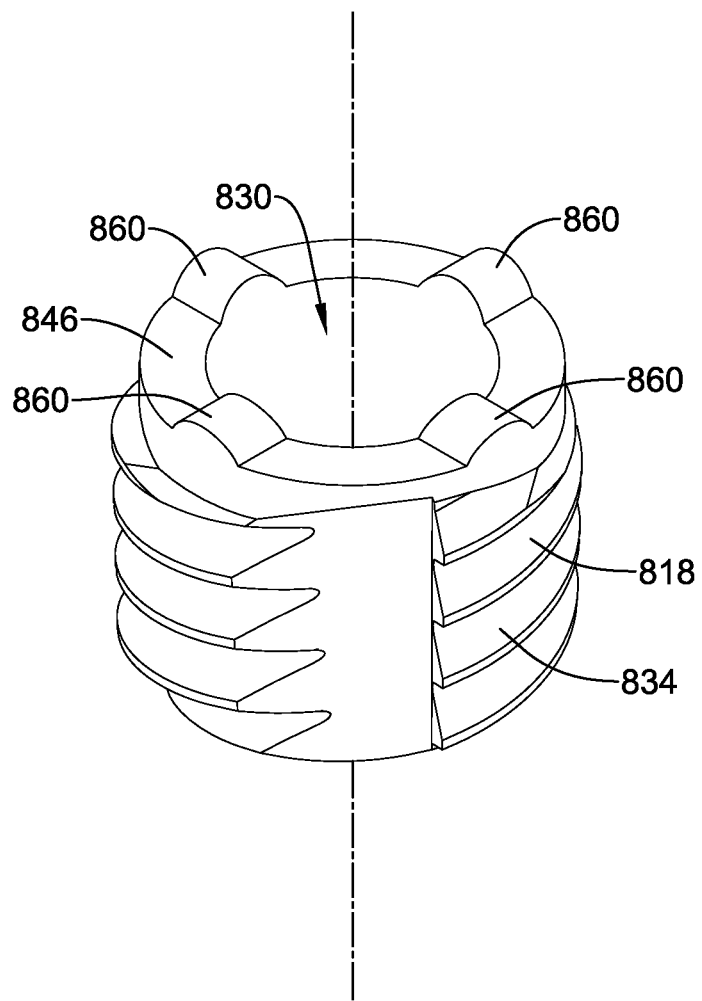
FIG. 14 is a perspective view of an alternative end cap of a modular dental implant configured to mate with the sleeve of FIG. 13.

For example, FIG. 13 is a perspective view of another alternative sleeve 820 of a modular dental implant which is configured to mate with an end cap 818, shown at FIG. 14, of the modular implant to prevent relative rotation therebetween. The sleeve 820 may include an upper surface 840, a lower surface 842, and a bore 838 extending therethrough from the upper surface 840 to the lower surface 842. The end cap 818, which may be similar to the end cap 18, may be securable to the core 16 of the body portion 12 proximate the apical end 24 of the implant 10 to retain the sleeve 820 between the head portion 14 and the end cap 818. For example, the end cap 818 may include a bore 830 extending therein or therethrough for receiving the smaller diameter portion 28 of the core 16 therein. The end cap 818 may be secured to the core 16 by a threaded connection, press fit, adhesive, welding, diffusion bonding, sintering, crimping, swaging, fasteners, or similar mechanisms.

The end cap 818 may include external threads 834 for engaging bone. In some embodiments the threads 834 may be self-tapping threads. The threads 834 may provide initial stability of the implant 10 when implanted in a bone prior to osseointegration in some instances.

The upper surface 840 of the sleeve 820 may be configured to mate with or abut the lower surface 44 of the head portion 14 of the body portion 12 of the implant 10. In such an embodiment, the lower surface 842 of the sleeve 820 may, alternatively or additionally, include a non-planar surface interacting with the upper surface 846 (which may include a non-planar surface) of the end cap 818 to prevent rotation of the sleeve 820 relative to the core 16 of the body portion 12. For instance, as shown in FIG. 13, the lower surface 842 of the sleeve 820 may include one or more, or a plurality of divots or indentations 852 extending toward the coronal end 22 of the implant 10 relative to other portions of the lower surface 842. The indentations 852, which may be positioned at desired intervals around the circumference of the sleeve 820, may be configured to interact with complementary tabs, bumps or projections 860 in the upper surface 846 of the end cap 818. The indentations 852 being portions of the lower surface 842 which are closer to the proximal or coronal end 22 of the implant 10 than other portions of the lower surface 842 which are closer to the distal or apical end 24 of the implant 10. The mating relationship between indentations 852 of the sleeve 820 with cooperating tabs, bumps or projections 860 in the upper surface 846 of the end cap 818 may prevent rotation of the sleeve 820 relative to the core 16 of the body portion 12 when assembled. Accordingly, portions of the sleeve 820 may be closer to the apical end 24 of the implant 10 than portions of the end cap 818, and likewise, portions of the end cap 818 may extend closer to the coronal end 22 of the implant 10 than portions of the sleeve 820.

Accordingly, it is contemplated that the lower surface of the sleeve 820 may alternatively include one or more alternative anti-rotation features, as described herein, configured to interact and mate with one or more anti-rotation features of the upper surface 846 of the end cap 818 which prevent rotation of the sleeve 820 about the central longitudinal axes of the body portion 12 and sleeve 820 relative to the core 16 of the body portion 12.

Those skilled in the art will recognize that the present invention may be manifested in a variety of forms other than the specific embodiments described and contemplated herein. Accordingly, departure in form and detail may be made without departing from the scope and spirit of the present invention as described in the appended claims.

What is claimed is:

1. A modular dental implant comprising:
   a body portion including head portion and a reduced diameter core extending from the head portion, the body portion having a central longitudinal axis, the head portion including one or more recesses each having an inner surface extending longitudinally and at least two side surfaces extending longitudinally, the core including a first portion and a second portion apical of the first portion, the second portion having a second diameter that is smaller than a first diameter of the first portion and the head portion includes threaded lands alternatingly arranged circumferentially between the one or more recesses of the head portion; and
   a sleeve including a bore extending therethrough from an upper surface of the sleeve to a lower surface of the sleeve, the sleeve positionable around the reduced diameter core of the body portion with the upper surface of the sleeve facing the head portion, the sleeve having a first section configured to abut the inner surface of each of the one or more recesses of the head portion and a second section configured to abut at least an apical end of the first portion of the core, wherein the sleeve includes one or more fingers extending into and engaging the inner surface of each of the one or more recesses, a cross-section of the modular dental implant taken perpendicular to the central longitudinal axis includes one or more portions of the head portion alternatingly arranged with one or more portions of the sleeve circumferentially about the central longitudinal axis radially outward of an outer diameter of the core;
   wherein the upper surface of the sleeve is configured to be bound by the inner surface and the at least two side surfaces of the one or more recesses, such that rotation of the sleeve relative to the central longitudinal axis of the body portion is prevented; and
   wherein the upper surface of the sleeve and the one or more recesses of the head portion are positioned along a bone engaging portion of the head portion.

2. The modular dental implant of claim 1, wherein the sleeve is formed of a porous metal material to promote ingrowth of bone or soft tissue.

3. The modular dental implant of claim 1, wherein the upper surface of the sleeve and the one or more recesses of the head portion are positioned in a tissue-growth-promoting region of the implant.

4. The modular dental implant of claim 1, wherein the threaded lands extend closer to an apical end of the dental implant than the upper surface of the sleeve including the one or more fingers.

5. A modular dental implant comprising:
   a body portion including a head portion and a reduced diameter core extending from the head portion, the body portion having a central longitudinal axis, the head portion including one or more recesses each having an inner surface extending longitudinally, wherein the head portion includes threaded lands alternatingly arranged circumferentially between the one or more recesses of the head portion; and
   a sleeve including a bore extending therethrough from an upper surface of the sleeve to a lower surface of the sleeve, the sleeve positionable around the reduced diameter core of the body portion with the upper surface of the sleeve facing the head portion, wherein the sleeve includes one or more fingers extending into and engaging the inner surface of each of the one or more recesses;
   wherein the upper surface of the sleeve is configured to prevent rotation of the sleeve relative to the central longitudinal axis of the body portion;
   wherein a cross-section of the modular dental implant taken perpendicular to the central longitudinal axis includes one or more portions of the head portion alternatingly arranged with one or more portions of the sleeve circumferentially about the central longitudinal axis radially outward of an outer diameter of the core.

6. The modular dental implant of claim 5, wherein the threaded lands extend closer to an apical end of the dental implant than the upper surface of the sleeve including the one or more fingers.

7. The modular dental implant of claim 5, wherein the sleeve is formed of a porous metal material to promote ingrowth of bone or soft tissue.

8. A modular dental implant comprising:
a body including a head portion and a reduced diameter core extending from the head portion, the core including a first portion having a first diameter and a second portion apical of the first portion having a second diameter smaller than the first diameter, the body having a central longitudinal axis, the head portion including a threaded upper portion and a lower portion having a threaded region and one or more recesses each having an inner surface extending longitudinally, the threaded upper portion and the threaded region having different threading, wherein the head portion includes threaded lands alternatingly arranged circumferentially between the one or more recesses of the head portion;
a sleeve including a bore extending therethrough from an upper surface of the sleeve to a lower surface of the sleeve, the sleeve positionable around the first portion of the core such that the upper surface of the sleeve faces a lower surface of the head portion of the body, the sleeve having a first section configured to abut the inner surface of each of the one or more recesses of the head portion and a second section configured to abut at least an apical end of the first portion of the core, wherein the sleeve includes one or more fingers extending into and engaging the inner surface of each of the one or more recesses, a cross-section of the modular dental implant taken perpendicular to the central longitudinal axis includes one or more portions of the head portion alternatingly arranged with one or more portions of the sleeve circumferentially about the central longitudinal axis radially outward of an outer diameter of the cores; and
an end cap attached to the second portion of the core such that the sleeve is captured between the head portion and the end cap;
wherein the modular dental implant is configured to prevent rotation of the sleeve about the central longitudinal axis of the body relative to the core of the body; and
wherein the upper surface of the sleeve and the one or more recesses of the head portion are configured to be positioned along a bone engaging portion of the head portion.

9. The modular dental implant of claim 8, wherein the upper surface of the sleeve and the lower surface of the head portion of the body are located apical of at least a portion of the threaded region.

10. The modular dental implant of claim 8, wherein the sleeve is formed of a porous metal material to promote ingrowth of bone or soft tissue.

11. The modular dental implant of claim 8, wherein the threaded lands extend closer to an apical end of the dental implant than the upper surface of the sleeve including the one or more fingers.

12. A method of assembling a modular dental implant, the method comprising:
providing a body including a head portion and a reduced diameter core extending from the head portion, the core including a first portion having a first diameter and a second portion having a second diameter smaller than the first diameter, the body having a central longitudinal axis, the head portion including a bone engaging portion and a plurality of recesses each having an inner surface extending longitudinally and located apical of at least a portion of the bone engaging portion;
advancing a sleeve over the first portion of the core such that an upper surface of the sleeve engages a lower surface of the head portion and contacts the inner surface of each recess of the plurality of recesses, the sleeve including a sleeve length equal to a length of the first portion; and
mating the upper surface of the sleeve with the lower surface of the head portion to prevent rotation of the sleeve relative to the core of the body by engaging threaded lands of the head portion with one or more fingers of the sleeve, the threaded lands alternatingly arranged circumferentially between the plurality of recesses of the head portion, the one or more fingers extending into and engaging the inner surface of each of the plurality of recesses, a cross-section of the modular dental implant taken perpendicular to the central longitudinal axis includes one or more portions of the head portion alternatingly arranged with one or more portions of the sleeve circumferentially about the central longitudinal axis radially outward of an outer diameter of the core.

13. The method of claim 12, wherein the upper surface of the sleeve and the lower surface of the head portion are positioned along a bone engaging portion of the head portion.

14. The modular dental implant of claim 12, wherein the sleeve is formed of a porous metal material to promote ingrowth of bone or soft tissue.

15. The modular dental implant of claim 12, wherein the threaded lands extend closer to an apical end of the dental implant than the upper surface of the sleeve including the one or more fingers.

* * * * *

UNITED STATES PATENT AND TRADEMARK OFFICE
CERTIFICATE OF CORRECTION

PATENT NO. : 9,433,480 B2
APPLICATION NO. : 12/974830
DATED : September 6, 2016
INVENTOR(S) : Steven Pelote It is certified that error appears in the above-identified patent and that said Letters Patent is hereby corrected as shown below:

In the Claims

In Column 11, Line 58, in Claim 1, after "including", insert --a--, therefor

Signed and Sealed this
Sixth Day of March, 2018

Andrei Iancu
*Director of the United States Patent and Trademark Office*